United States Patent
Hagi (10) Patent No.: US 10,238,289 B2
(45) Date of Patent: Mar. 26, 2019

(54) BODY FLUID COMPONENT MEASURING SYSTEM

(71) Applicant: TERUMO KABUSHIKI KAISHA, Shibuya-ku (JP)

(72) Inventor: Kouji Hagi, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 860 days.

(21) Appl. No.: 14/035,022

(22) Filed: Sep. 24, 2013

(65) Prior Publication Data

US 2014/0024908 A1    Jan. 23, 2014

Related U.S. Application Data

(63) Continuation of application No. PCT/JP2011/006947, filed on Dec. 13, 2011.

(30) Foreign Application Priority Data

Mar. 25, 2011    (JP) .................................. 2011-068627

(51) Int. Cl.
*A61B 5/1459*    (2006.01)
*A61B 5/145*    (2006.01)
*A61B 5/00*    (2006.01)

(52) U.S. Cl.
CPC .......... *A61B 5/0004* (2013.01); *A61B 5/0002* (2013.01); *A61B 5/1459* (2013.01);
(Continued)

(58) Field of Classification Search
CPC .......... A61B 2560/0412; A61B 5/0002; A61B 5/0004; A61B 5/14503; A61B 5/14532;
(Continued)

(56) References Cited

U.S. PATENT DOCUMENTS 5,507,288 A * 4/1996 Bocker ................ A61B 5/0002
  128/903
6,219,738 B1 * 4/2001 Kondo .................... G06F 13/36
  710/311

(Continued)

FOREIGN PATENT DOCUMENTS

| JP | 2002-526137 A | 8/2002 |
| JP | 2008-246204 A | 10/2008 |
| JP | 2009-229269 A | 10/2009 |

OTHER PUBLICATIONS

International Search Report (PCT/ISA/210) dated Feb. 28, 2012, by the Japanese Patent Office as the International Searching Authority for International Application No. PCT/JP2011/006947.

*Primary Examiner* — Navin Natnithithadha
(74) *Attorney, Agent, or Firm* — Buchanan Ingersoll & Rooney PC (57) ABSTRACT

A body fluid component measuring system which is capable of continuous measurement and reduces downtime includes a sensor unit which is positionable indwelling in the skin of a subject and which measures a predetermined body fluid component included in the body fluid of the subject; and a transmission unit which is detachably attached to the sensor unit and which calculates blood glucose level based on measurement data measured by the sensor unit, and transmits the calculated blood glucose level to a display unit. Identification information for establishing communication between the transmission unit and the display unit is stored in the sensor unit, and the transmission unit, upon activation, uses the identification information read out by the sensor unit to establish communication with the display unit.

15 Claims, 6 Drawing Sheets

(52) U.S. Cl.
CPC ...... *A61B 5/14503* (2013.01); *A61B 5/14532* (2013.01); *A61B 5/6833* (2013.01); *A61B 5/6848* (2013.01); *A61B 5/742* (2013.01); *A61B 5/7405* (2013.01); *A61B 2560/0412* (2013.01)

(58) Field of Classification Search
CPC ... A61B 5/1459; A61B 5/6833; A61B 5/6848; A61B 5/7405; A61B 5/742
See application file for complete search history.

(56) References Cited

U.S. PATENT DOCUMENTS

| | | | |
|---|---|---|---|
| 6,809,653 | B1 | 10/2004 | Mann et al. |
| 8,844,007 | B2* | 9/2014 | Vicente ................. A61B 5/002 726/6 |
| 2002/0065453 | A1* | 5/2002 | Lesho ................. A61B 5/14532 600/347 |
| 2007/0078323 | A1* | 4/2007 | Reggiardo ........... A61B 5/0002 600/347 |
| 2008/0092638 | A1* | 4/2008 | Brenneman ......... G06F 19/3418 73/61.41 |
| 2008/0242962 | A1 | 10/2008 | Roesicke et al. |
| 2009/0280745 | A1* | 11/2009 | Granqvist ............ A61B 5/0002 455/41.3 |
| 2010/0274515 | A1* | 10/2010 | Hoss .................. A61B 5/14532 702/104 |
| 2011/0193704 | A1* | 8/2011 | Harper ............... A61B 5/14532 340/573.1 |
| 2012/0004739 | A1* | 1/2012 | Sato ...................... H04L 12/282 700/7 |
| 2012/0123227 | A1* | 5/2012 | Sun .................... A61B 5/14532 600/309 |
| 2012/0260323 | A1* | 10/2012 | San Vicente .......... A61B 5/002 726/6 |

* cited by examiner

BODY FLUID COMPONENT MEASURING SYSTEM

CROSS REFERENCES TO RELATED APPLICATIONS

This application is a continuation of International Application No. PCT/JP2011/006947 filed on Dec. 13, 2011, and claims priority to Japanese Application No. 2011-068627 filed on Mar. 25, 2011, the entire content of both of which is incorporated herein by reference.

TECHNICAL FIELD

The present invention generally relates to body fluid component measuring systems for continuously measuring the body fluid of a subject, and displaying the concentration of a predetermined component included in the body fluid. More particularly, the present invention relates to a body fluid component measuring system for intermittently and continuously measuring the body fluid of a subject, and displaying a blood glucose level.

BACKGROUND DISCUSSION

Conventionally, so-called self-monitoring of blood glucose (SMBG), in which blood drawn by puncturing a fingertip or the like by a dedicated puncture device is measured by a blood glucose meter each time blood is drawn, has been widely used as a method for a diabetic to measure and manage the blood glucose level for himself/herself.

As an alternative, a body fluid component measuring system allowing continuous glucose monitoring (CGM), in which the blood glucose level of a subject is continuously monitored with a sensor positioned indwelling in a skin by making a puncture under the skin or the like with a needle disposed on a dedicated sensor unit, has recently been developed (see Japanese Application Publication No. 2002-526137, for example), and has already been put to practical use in Europe and America.

The body fluid component measuring system used for CGM includes: a sensor unit mounted on a subject at all times; a transmitting unit for transmitting a measurement signal in the sensor unit to the outside, the transmitting unit being attached to the sensor unit; and a display device for calculating a blood glucose level on the basis of the measurement signal transmitted from the transmitting unit and displaying the blood glucose level. The sensor unit is replaced with a new sensor unit with a frequency of about once every few days to once every week.

The transmitting unit and the display device are used continuously irrespective of replacement of the sensor unit, and can be used for a long period of time by repeating the charging or replacement of batteries.

However, it is not desirable to interrupt the continuous monitoring of the blood glucose level of the subject for a long period of time each time the batteries included in the transmitting unit and the display device are charged or replaced. On the other hand, the cumulative value of time during which the continuous monitoring of the blood glucose level is interrupted can be reduced by decreasing the frequency of charging or the frequency of replacement of the batteries included in the transmitting unit and the display device. In that case, however, the batteries included in the transmitting unit and the display device are increased in size, thus decreasing the convenience of the subject that wears the transmitting unit and the display device at all times.

SUMMARY

According to one aspect of the disclosure here, a body fluid component measuring system comprises: a display unit, a sensor unit and a transmitting unit. The sensor unit is attachable to a body of a subject and comprises: a needle possessing a point configured to be indwelled in skin of the subject when the sensor unit is attached to the body of the subject to obtain a body fluid sample of the subject; a component measuring section which is connected to the needle to receive the body fluid sample obtained by the needle and which measures a predetermined body fluid component of the body fluid sample; and a memory. The transmitting unit is detachably attachable to the sensor unit and comprises: memory storing a calculating program which calculates a concentration of the predetermined body fluid component included in the body fluid sample based on the predetermined body fluid component of the body fluid sample measured by the component measuring section; and a transmitting module which transmits a result of the calculation of the concentration of the predetermined body fluid component to the display device which displays the concentration of the predetermined body fluid component. The memory of the sensor unit stores identifying information, the transmitting unit reads the identifying information stored in the memory of the sensor unit, and the transmitting unit establishes communication with the display device using the identifying information read from the memory of the sensor unit.

According to another aspect, body fluid component measuring system comprises: a sensor unit configured to be at least partially positioned indwelling in skin of a subject, with the sensor unit measuring a predetermined body fluid component of a body fluid of the subject to obtain a measurement signal; and a transmitting unit detachably attachable to the sensor unit and activated by a user, with the transmitting unit performing calculation of a concentration of the body fluid component in a body fluid as a same kind as or a different kind from the body fluid on a basis of the measurement signal measured in the sensor unit, and transmitting a result of the calculation to a display device. The sensor unit stores identifying information for establishing communication between the transmitting unit and the display device, and the transmitting unit, when activated, reads the identifying information stored in the sensor unit and establishing communication with the display device using the read identifying information.

According to a further aspect, a method of measuring a body fluid component comprises: a transmitting unit reading communication identification information stored in a sensor unit, wherein the transmitting unit is detachably mounted on the sensor unit, the transmitting unit verifying that the communication identification information read from the sensor unit matches communication identification information in a display unit to establish communication between the transmitting unit and the display unit, with the display unit including a display which displays information; the sensor unit obtaining a body fluid sample of a subject which contains the body fluid component; the sensor unit measuring the body fluid component of the body fluid sample and sending measurement data to the transmitting unit indicating the measured body fluid component; and the transmitting unit calculating a concentration of the body fluid component based on the measurement data from the sensor unit.

The body fluid component measuring system and method disclosed here is able to shorten the time during which the monitoring of the concentration of a predetermined body fluid component is interrupted without impairing the convenience of the subject.

Other features and aspects of the system and method disclosed here will become more apparent from the following detailed description considered with reference to the accompanying drawings.

BRIEF DESCRIPTION OF DRAWINGS

The accompanying drawings, which are incorporated in and constitute a part of the specification, illustrate embodiments of the present invention and together with the description, serve to explain the principles of the present invention.

DETAILED DESCRIPTION

Embodiments of a body fluid component measurement system and method representing examples of the body fluid component measurement system and method disclosed here will be described in detail below with reference to the accompanying drawing figures.

<1. External Constitution of Body Fluid Component Measuring System>

Figure 1:
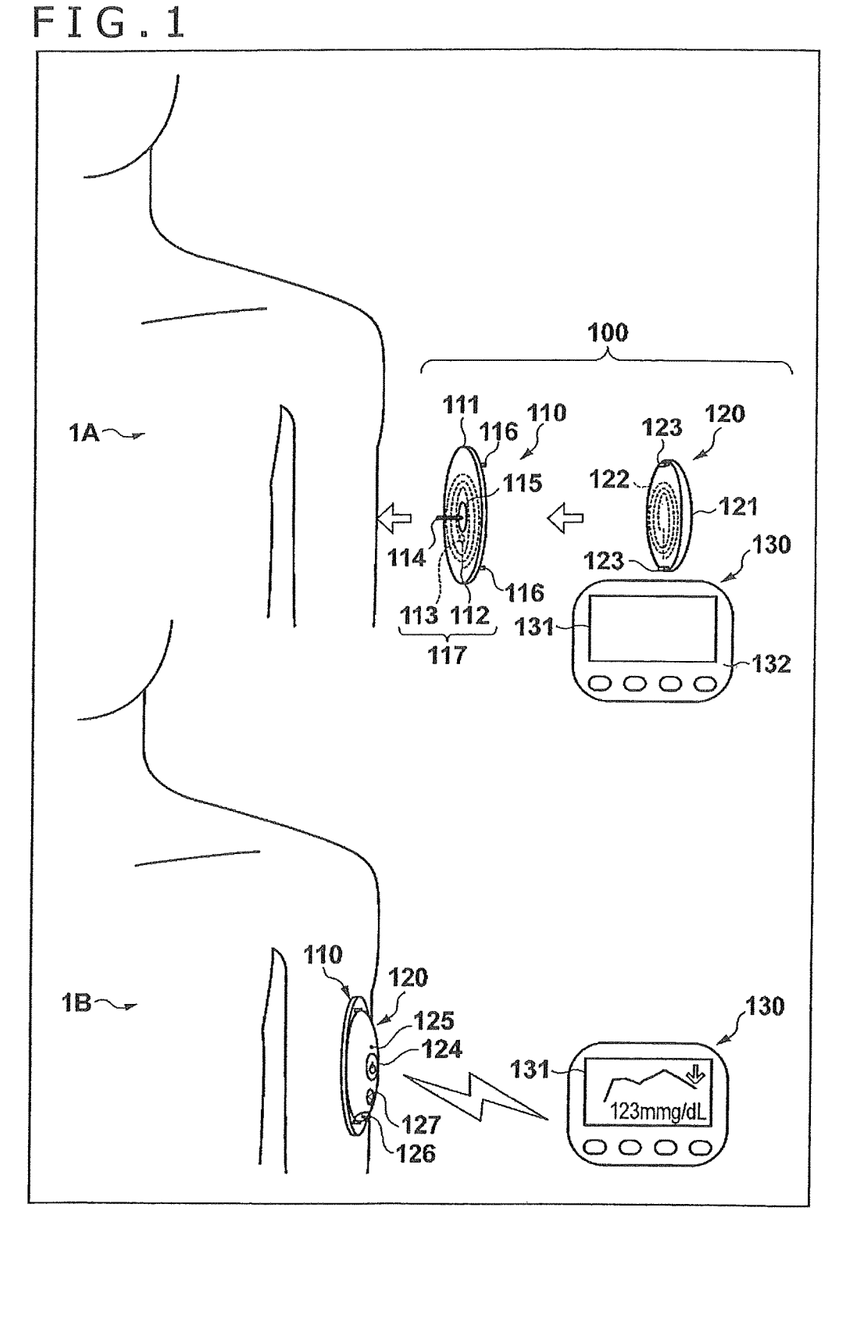
FIG. 1 is a schematic illustration showing an external constitution of a body fluid component measuring system according to one embodiment disclosed here.

FIG. 1 illustrates the external constitution of a body fluid component measuring system 100 according to one embodiment disclosed here. As shown in 1A of FIG. 1, the body fluid component measuring system 100 includes a sensor unit 110, a transmitting unit 120, and a display unit 130.

A main body portion 111 is constructed in a liquid-tight manner or structure of hard plastic, metal, ceramic, or the like that can prevent liquids from infiltrating or penetrating. Examples of the hard plastic include an ABS resin, polypropylene, polycarbonate, and a flexible resin such as polyurethane or the like. Examples of the metal include SUS and titanium. Examples of the ceramic include zirconia and the like. A skin sticking tape (adhesive tape) having a waterproof function is disposed on the bottom surface of the main body portion 111. Therefore the sensor unit 110 can be stuck or adhered directly to an upper arm region, an abdominal region, or the like of a subject and held at such position by the adhesive.

Further, a needle 114 to be positioned indwelling in the skin of the subject and to come into contact with a body fluid under the skin is provided on, and projects from, the bottom surface of the main body portion 111, and is connected to a component measuring section 115 disposed within the main body portion 111. The component measuring section 115 outputs a measurement signal corresponding to the quantity of a predetermined body fluid component such as glucose, lactic acid, or the like in an interstitial fluid as the body fluid under the skin with which body fluid the needle 114 comes into contact.

An IC tag 117 with a built-in A/D circuit (hereinafter referred to simply as an IC tag 117), which IC tag includes an antenna 112 and an IC (integrated circuit) chip 113 is provided inside the main body portion 111. The IC tag 117 operates on an electromotive force produced by an electromagnetic field generated in the transmitting unit 120 as power, to control measurement by the component measuring section 115, and transmit measurement data (digital data converted from analog data) obtained as a result of the measurement to the transmitting unit 120. That is, the component measuring section 115 outputs a measurement signal to the IC tag 117, the IC tag 117 converts a measurement signal (analog data) to measurement data (digital data) and transmits the measurement data to the transmitting unit 120.

The transmitting unit 120 includes a housing 121. An IC tag transmitting and receiving module 122 is disposed inside the housing 121, which module 122 generates the electromagnetic field for the IC tag 117 of the sensor unit 110 by being driven and supplies power to the IC tag 117 by electromagnetic induction, and receives measurement data indicating a measurement result by detecting changes in an electromagnetic field generated by the IC tag 117. The transmitting unit 120 is configured to process the measurement data received from the sensor unit 110, calculate the concentration of a predetermined body fluid component included in a body fluid such as a blood glucose level or the like (concentration of the predetermined body fluid component in a body fluid that is the same kind as or a different kind from the body fluid), and thereafter store the calculated concentration of the predetermined body fluid component such as the blood glucose level or the like within a memory of the IC chip 113 in association with the date and time of the measurement via the IC tag transmitting and receiving module 122. The reference to calculating the concentration of the predetermined body fluid component in a body fluid that is the same kind as or a different kind from the body fluid refers to, for example, in the case of blood glucose level, the body fluid that is the same kind as the body fluid which is a measurement object is blood. An example of a body fluid that is a different kind from the body fluid which is a measurement object is interstitial fluid.

In addition, locking portions 123 are provided at the bottom surface of the housing 121. The locking portions 123 are configured to lock to the locking portions 116 at the back surface of the main body portion 111, whereby the transmitting unit 120 is detachably attachable to the sensor unit 110.

The display unit 130 includes a display region 131, and displays the concentration of the body fluid component (e.g., blood glucose level), which concentration is read from the sensor unit 110 and transmitted to the display unit 130 by the transmitting unit 120 on the basis of an instruction from an input section 132. The display unit 130 also includes the input section 132 which permits various kinds of operations for changing display contents displayed in the display region 131, input of predetermined information, and the like.

1B of FIG. 1 shows a state in which the transmitting unit 120 is attached to the sensor unit 110. As shown in 1B of FIG. 1, a power switch 124 for turning on/off power to the transmitting unit 120 is provided at the back surface of the transmitting unit 120. Pressing the power switch 124 once turns on the power, and turns on a lamp 125. Further pressing the power switch 124 one more time turns off the power, and turns off the lamp 125.

A speaker 127 is further provided at the back surface of the transmitting unit 120. The speaker 127 outputs sound (audible notifications) to the subject when an error or the like is detected in the transmitting unit 120, for example. A charging connector 126 is also provided at the back surface of the transmitting unit 120. A secondary battery (rechargeable battery) incorporated in the transmitting unit 120 can be charged by connecting the charging connector 126 to a charging adapter.

With the construction described above, when the power to the transmitting unit 120 is turned on by pressing the power switch 124 in the state in which the transmitting unit 120 is attached to the sensor unit 110, the concentration of the predetermined body fluid component in each predetermined cycle can be viewed on the display unit 130 (the display unit 130 in 1B of FIG. 1 displays the concentration of the body fluid component which concentration is obtained by a present measurement together with a trend graph in the display region 131).

<2. Functional Configuration of Body Fluid Component Measuring System>

The configuration of the body fluid component measuring system 100, including a functional configuration of the body fluid component measuring system 100, will next be described with reference to FIG. 2. Features and elements in FIG. 2 corresponding to features and elements already described above concerning the external constitution shown in 1A and 1B of FIG. 1 are identified by the same reference numerals.

Figure 2:
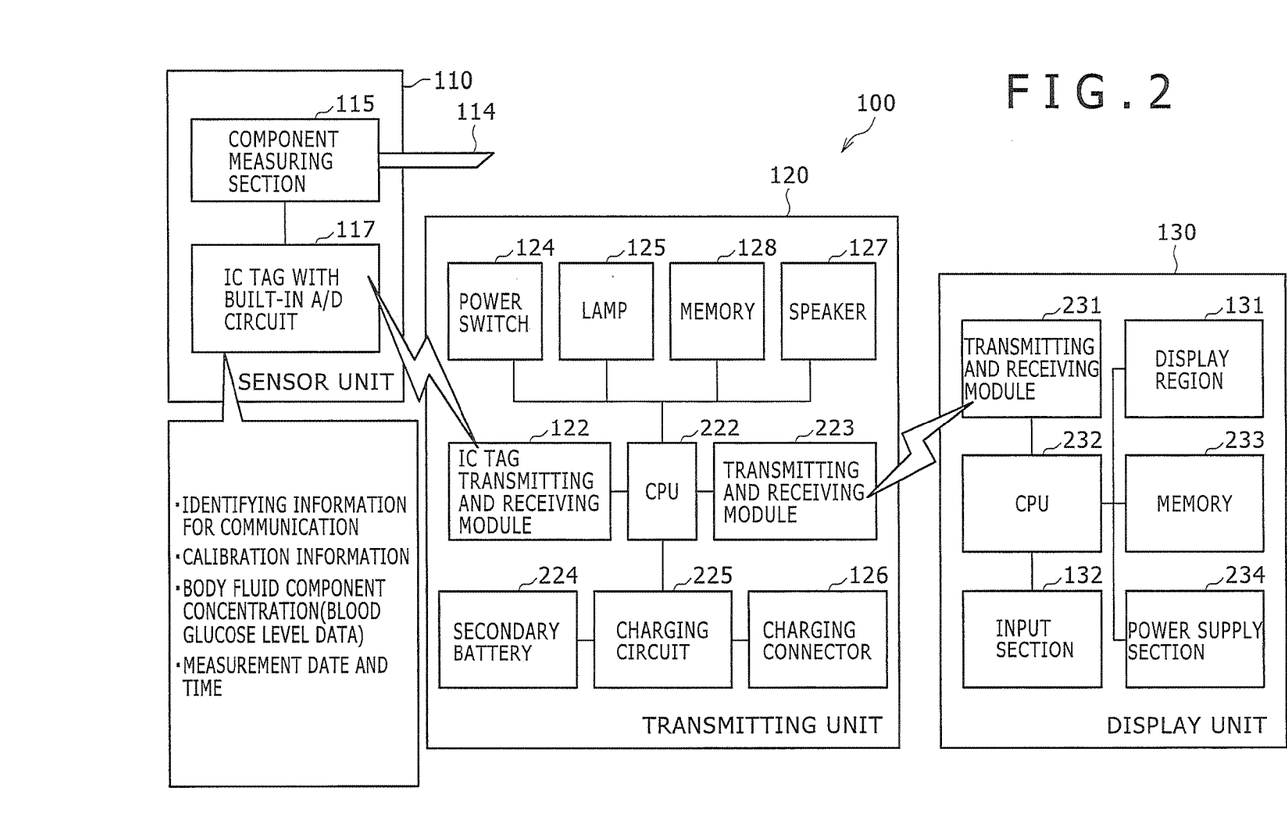
FIG. 2 is a block diagram showing the configuration, including the functional configuration, of the body fluid component measuring system.

As shown in FIG. 2, the sensor unit 110 includes the needle 114, the component measuring section 115, and the IC tag 117. The needle 114 is a capillary tube for drawing and guiding body fluid (body fluid sample) so that the body fluid reaches the component measuring section 115, and is set to a length such that the point of the needle 114 reaches under the skin of the subject. The needle 114 is connected to the component measuring section 115, and guides the body fluid into the component measuring section 115. The component measuring section may be disposed in the vicinity of the point of the needle 114 so that the body fluid component is measured under the skin of the subject.

The component measuring section 115 is a measuring means for measuring the concentration of the predetermined body fluid component (for example glucose, uric acid, cholesterol, protein, a mineral, blood cells, or the like) included in the body fluid, and performs measurement using a well-known measuring method. Examples of the component measuring section 115 include an LED, a photodiode and a fluorescent dye. The body fluid guided through the needle 114 includes blood, interstitial fluid, lymph, and the like. The measuring method includes a method of measuring fluorescence intensity when a fluorescent dye capturing the predetermined body fluid component included in the body fluid as a measurement object is irradiated with exciting light, a method of optically or electrochemically measuring the predetermined body fluid component included in the body fluid as a measurement object using an oxidase, and the like.

It is to be noted that the body fluid component measuring system according to the present embodiment is configured to measure glucose concentration in an interstitial fluid with the needle 114 indwelling under the skin, and convert the glucose concentration in the interstitial fluid into glucose concentration in blood (blood glucose level). In addition, examples of a measuring sensor include a fluorescence sensor in which a boronic acid group-introduced fluorescent dye that binds to a saccharide and exhibits a Stokes shift is fixed to a hydrogel, a GOD sensor using a glucose oxidase (GOD) and an oxidation-reduction electrode with the GOD fixed to the electrode. The needle 114 can also puncture a blood vessel rather than under the skin so that glucose concentration in blood is measured directly.

The IC tag 117 controls the component measuring section 115 by the electromotive force produced by the electromagnetic field generated in the transmitting unit 120. In addition, the IC tag 117 transmits digital measurement data obtained by subjecting a measurement result from the component measuring section 115 to A/D conversion to the transmitting unit 120.

The memory (schematically identified as "M" in the IC chip 117 shown in FIG. 2) of the IC chip 113 forming the IC tag 117 stores communication identifying information used in communication between a transmitting and receiving module 223 of the transmitting unit 120 and a transmitting and receiving module 231 of the display unit 130 to be described later. In addition, the memory of the IC chip 113 forming the IC tag 117 stores the concentration of the body fluid component such as the blood glucose level or the like calculated in the transmitting unit 120 on the basis of the measurement data transmitted to the transmitting unit 120 in association with the date and time of the measurement. Further, the memory of the IC chip 113 forming the IC tag 117 stores calibration information used when the transmitting unit 120 calculates the concentration of the body fluid component such as the blood glucose level or the like. The calibration information stored in the memory of the IC chip 113 is transmitted together with the measurement data when the measurement data is transmitted to the transmitting unit 120.

The transmitting unit 120 includes the power switch 124, the lamp 125, a memory 128, the speaker 127, the IC tag transmitting and receiving module 122, a central processing unit (CPU) 222, the transmitting and receiving module 223, a secondary battery 224, a charging circuit 225, and a charging connector 126. The CPU 222 includes a ROM storing a control program executed by the CPU 222 and various kinds of data, a RAM for primary storage of various kinds of data as a work area, and the like. The CPU 222 functions as a control section for performing processing and making decisions in each process.

When the power switch 124 is pressed, the power to the transmitting unit 120 is turned on, and the lamp 125 is turned on. The lamp 125 may be configured to notify the user that there is only a small amount of charge remaining in the secondary battery 224 by blinking when the amount of charge remaining in the secondary battery 224 has decreased. In addition, the lamp 125 may be configured to illuminate in different colors according to an internal state of the transmitting unit 120 (for example the lamp 125 may be configured to illuminate in green in a normal state, and illuminate in red when an abnormality is detected).

The memory 128 stores a calculating program for calculating the concentration of the predetermined body fluid component included in the body fluid on the basis of the digital measurement data as the measurement result received from the sensor unit 110 and the calibration information, a calibrating program for calculating the calibration information used when the concentration of the body fluid component is calculated, a control program for controlling the operation of the whole of the transmitting unit 120, and the like.

The calculating program is prepared for different body fluids as a measurement object (for example, blood, interstitial fluid, lymph, or the like) and for different body fluid components as a calculation object (for example, glucose, uric acid, cholesterol, protein, a mineral, blood cells, or the like). The transmitting unit 120 can thereby calculate the concentrations of various body fluid components.

The speaker 127 provides notification of the end of measurement, the concentration of the measured body fluid component, or the like by sound. For example, the speaker 127 outputs a short beep sound when the blood glucose level obtained as a result of measurement is normal, and continuously outputs a louder warning sound than in the normal case when the blood glucose level obtained as a result of measurement is abnormal.

The IC tag transmitting and receiving module 122 is provided to supply power and transmit and receive various kinds of information between the transmitting unit 120 and the sensor unit 110. The CPU 222 controls the operation of the whole of the transmitting unit 120. The transmitting and receiving module 223 is a communication module for transmitting the concentration of the body fluid component and the corresponding measurement date and time, which are read from the sensor unit 110 using the IC tag transmitting and receiving module 122, to the display unit 130 on the basis of an instruction from the display unit 130.

The secondary battery 224 supplies power to various parts forming the transmitting unit 120. The charging circuit 225 is a circuit for charging the secondary battery 224. The charging circuit 225 charges the secondary battery 224 when supplied with power from an adapter connected to the charging circuit 225 via the charging connector 126.

The display unit 130 includes a transmitting and receiving module 231, a CPU 232, the input section 132, the display region 131, a memory 233, and a power supply section 234. The CPU 232 includes a ROM storing a control program executed by the CPU 232 and various kinds of data, a RAM for primary storage of various kinds of data as a work area, and the like. The CPU 232 functions as a control section for performing processing and making decisions in each process.

The transmitting and receiving module 231 receives the concentration of the body fluid component which concentration is transmitted from the transmitting unit 120 via the transmitting and receiving module 223. The concentration of the body fluid component which concentration is received in the transmitting and receiving module 231 is processed in the CPU 232, displayed in the display region 131, and stored in the memory 233.

The input section 132 is a button and the like for receiving input instructions of the subject. The input section 132 is used for instruction operations to turn on power to the display unit 130, an instruction given to the transmitting unit 120 to call up the concentration of the body fluid component which concentration was calculated in the past, an instruction to change display, and information input for calculating the calibration information used when the concentration of the body fluid component is calculated, and the like. The display region 131 and the input section 132 may be formed as a single part such as a touch panel or the like. The power supply section 234 is a battery for supplying power to various parts forming the display unit 130.

<3. Method of Use of Body Fluid Component Measuring System>

A method of use of the body fluid component measuring system 100 according to the present embodiment will next be described with reference to FIG. 3. In the following, for purposes of simplifying the description, the description will be set forth taking a blood glucose level as an example of the concentration of the body fluid component which concentration is calculated in the transmitting unit.

As described above, the body fluid component measuring system 100 according to the present embodiment includes the sensor unit 110, the transmitting unit 120, and the display unit 130. Of the units, the transmitting unit 120 is detachably attached to the sensor unit 110, and is desirably light and small for the subject. On the other hand, the transmitting unit 120 needs to be provided with a power supply sufficient to supply power necessary for measurement to the sensor unit 110 and to provide power for performing communication with the display unit 130.

From such a viewpoint, the body fluid component measuring system 100 according to the present embodiment is provided with a plurality of transmitting units, and is configured to include, interchange and use a transmitting unit which is being used and a transmitting unit which is being charged alternately. Specifically, two transmitting units, that is, a transmitting unit A and a transmitting unit B are prepared as transmitting units 120. In a state in which one of the transmitting units is attached to the sensor unit 110, the other transmitting unit is charged by a charging adapter. In a state in which one of the transmitting units is being charged, the other transmitting unit is attached to the sensor unit 110.

Such a construction can minimize the capacity of the secondary batteries included in the transmitting unit A and the transmitting unit B (that is, can reduce the size of the secondary batteries), and inhibits or prevents the convenience of the subject from being impaired. In addition, continuous monitoring of the blood glucose level is interrupted only when the transmitting unit A and the transmitting unit B are interchanged with each other, so that a time during which the continuous monitoring of the blood glucose level is interrupted can be shortened.

Figure 3:
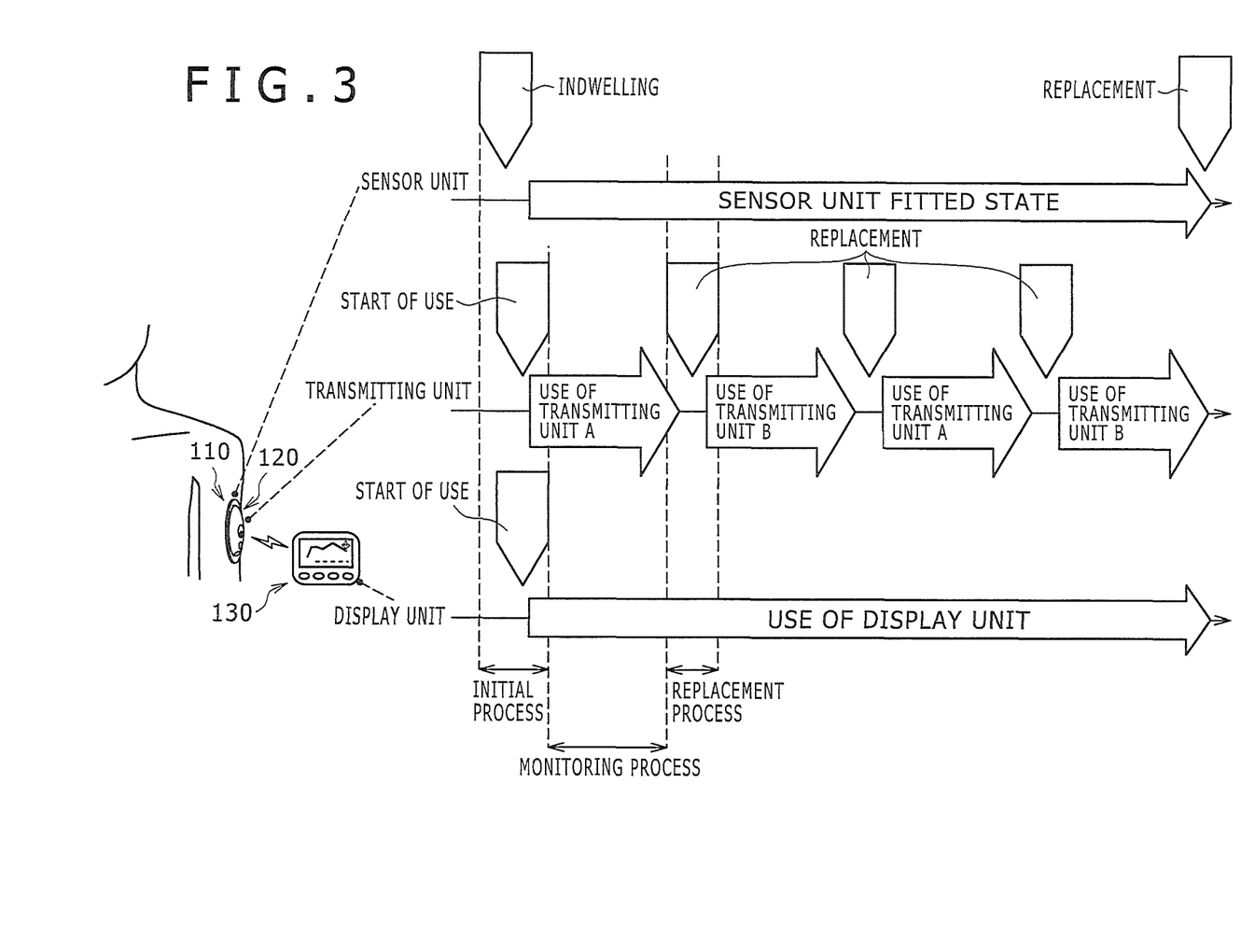
FIG. 3 is a diagram explaining a method of using parts forming the body fluid component measuring system.

FIG. 3 is a diagram showing an example in which the body fluid component measuring system 100 according to the present embodiment is used by such a use method. As shown in FIG. 3, because such a use method is adopted in the body fluid component measuring system 100, there are three process states (an initial process state, a monitoring process state, and a replacement process state).

In the initial process, when power to the transmitting unit 120 is turned on after the sensor unit 110 (name of the sensor unit: sensor unit A) is positioned indwelling in the skin of the subject and the transmitting unit 120 (name of the transmitting unit: transmitting unit A) is attached to the sensor unit 110, communication between the transmitting unit 120 (name of the transmitting unit: transmitting unit A) and the display unit 130 is established. Details of the initial process will be described later.

After the communication between the transmitting unit 120 and the display unit 130 is established in the initial process, the transmitting unit 120 starts a blood glucose level monitoring process. During the monitoring process, the sensor unit 110 performs measurement on the basis of an instruction from the CPU 222 which instruction is based on the program for calculating the concentration of the body fluid component, which program is stored in the memory 128 in the transmitting unit 120. In addition, the transmitting unit 120 reads blood glucose level data calculated on the basis of measurement data and stored in the sensor unit 110 from the sensor unit 110 and transmits the blood glucose level data to the display unit 130 on the basis of an instruction from the CPU 232 in the display unit 130, so that the blood glucose level data is displayed on the display unit 130. Details of the monitoring process will also be described later.

As the secondary battery of the transmitting unit 120 (name of the transmitting unit: transmitting unit A) is being exhausted with the amount of charge remaining in the secondary battery decreasing, the subject changes to the transmitting unit 120 (name of the transmitting unit: transmitting unit B) whose charging has been completed in advance. Details of the replacement process will also be described later.

After the replacement process is completed, the transmitting unit 120 (name of the transmitting unit: transmitting unit B) is attached to the sensor unit 110, and communication between the transmitting unit 120 (name of the transmitting unit: transmitting unit B) and the display unit 130 is established, the transmitting unit 120 (name of the transmitting unit: transmitting unit B) starts a blood glucose level monitoring process. As described above, during the monitoring process, the sensor unit 110 performs measurement on the basis of an instruction from the CPU 222 in the transmitting unit 120. In addition, the transmitting unit 120 reads blood glucose level data calculated on the basis of measurement data and stored in the sensor unit 110 from the sensor unit 110 and transmits the blood glucose level data to the display unit 130 on the basis of an instruction from the CPU 232 in the display unit 130, so that the blood glucose level data is displayed on the display unit 130.

While the monitoring process is performed by the transmitting unit 120 (name of the transmitting unit: transmitting unit B), the transmitting unit 120 (name of the transmitting unit: transmitting unit A) is connected to the charging adapter, and is charged. The monitoring process is thereafter continued until a time of replacement of the sensor unit 110 while the interchange of the transmitting unit 120 (name of the transmitting unit: transmitting unit A) and the transmitting unit 120 (name of the transmitting unit: transmitting unit B) is repeated.

The sensor unit 110 performs measurement on the basis of an instruction from the CPU 222 which instruction is based on the program for calculating the concentration of the body fluid component, which program is stored in the memory 128 in the transmitting unit 120, and blood glucose level data calculated in the transmitting unit 120 on the basis of measurement data is stored in the sensor unit 110. Thus, the display unit 130 does not need to be mounted in an operational state in the vicinity of the transmitting unit 120 at all times during the monitoring process. That is, the monitoring process is not interrupted even when power to the display unit 130 is off. One display unit 130 therefore suffices.

Referring again to FIG. 3, when a time of replacement of the sensor unit 110 arrives, the sensor unit 110 is replaced, and a new sensor unit 110 is positioned indwelling in the skin of the subject. In this case, the transmitting unit and the display unit that have been used thus far continue being used as the transmitting unit 120 (name of the transmitting unit: transmitting unit A or transmitting unit B) and the display unit 130. However, because the sensor unit 110 is replaced, the initial process is performed again.

Thus, in the body fluid component measuring system 100 according to the present embodiment, a plurality of transmitting units 120 are prepared, and use and charge thereof are repeated alternately. It is thereby possible to reduce the weight and size of the transmitting units 120 and shorten the time of interruption of the monitoring process.

<4. Functions for Realizing Above-Described Use Method in Body Fluid Component Measuring System>

Set forth next is a description of functions of various parts for realizing the method of using the body fluid component measuring system 100 according to the present embodiment, which method has been described above (in part 3.).

As described with reference to FIG. 3, each time the amount of charge remaining in the secondary battery of the transmitting unit 120 is decreased, the transmitting unit 120 is replaced with another transmitting unit 120. Therefore, at the time of the replacement process, it is inconvenient for the subject to be made to perform processes performed in the initial process again (a process of inputting information necessary to calculate calibration information, a process of setting information necessary to establish communication between the transmitting unit and the display unit, and the like). In addition, a workload on the subject is increased when blood glucose level data calculated on the basis of measurement data is read from a replaced transmitting unit again.

In other words, the time of interruption of the monitoring process can be further shortened by reducing the workload on the subject at the time of the replacement process. From such a viewpoint, the body fluid component measuring system 100 according to the present embodiment has the following functions.

A function of inheriting calibration information calculated during the indwelling time of the sensor unit 110 to a next transmitting unit 120 at the time of replacement of a transmitting unit 120.

A function of inheriting blood glucose level data calculated in the transmitting unit 120 on the basis of a result of measurement in the sensor unit 110 to the next transmitting unit 120 at the time of replacement of the transmitting unit 120 (function for enabling blood glucose level data calculated at a time of measurement before the replacement of the transmitting unit to be read from the transmitting unit after the replacement on the basis of an instruction from the display unit 130 irrespective of the replacement of the transmitting unit 120).

A function for enabling the transmitting unit 120 after replacement to establish communication with the display unit 130 immediately in a case where the sensor unit 110 is not replaced but only the transmitting unit 120 is replaced.

In order to realize the above functions under the above method of use, the body fluid component measuring system 100 according to the present embodiment is configured such that a memory is provided to or as a part of the sensor unit 110 and the various kinds of information to be inherited to the next transmitting unit 120 at the time of the replacement of the transmitting unit 120 are stored in the memory.

With such a configuration, when the transmitting unit 120 is attached to the sensor unit 110 and the power to the transmitting unit 120 is turned on in the replacement process, the transmitting unit 120 can read the various kinds of information from the sensor unit 110 as required, and the above functions can be realized. Description will be made in the following of a process flow for realizing the above functions in respective process states.

<5. Flow of Initial Process>

Figure 4:
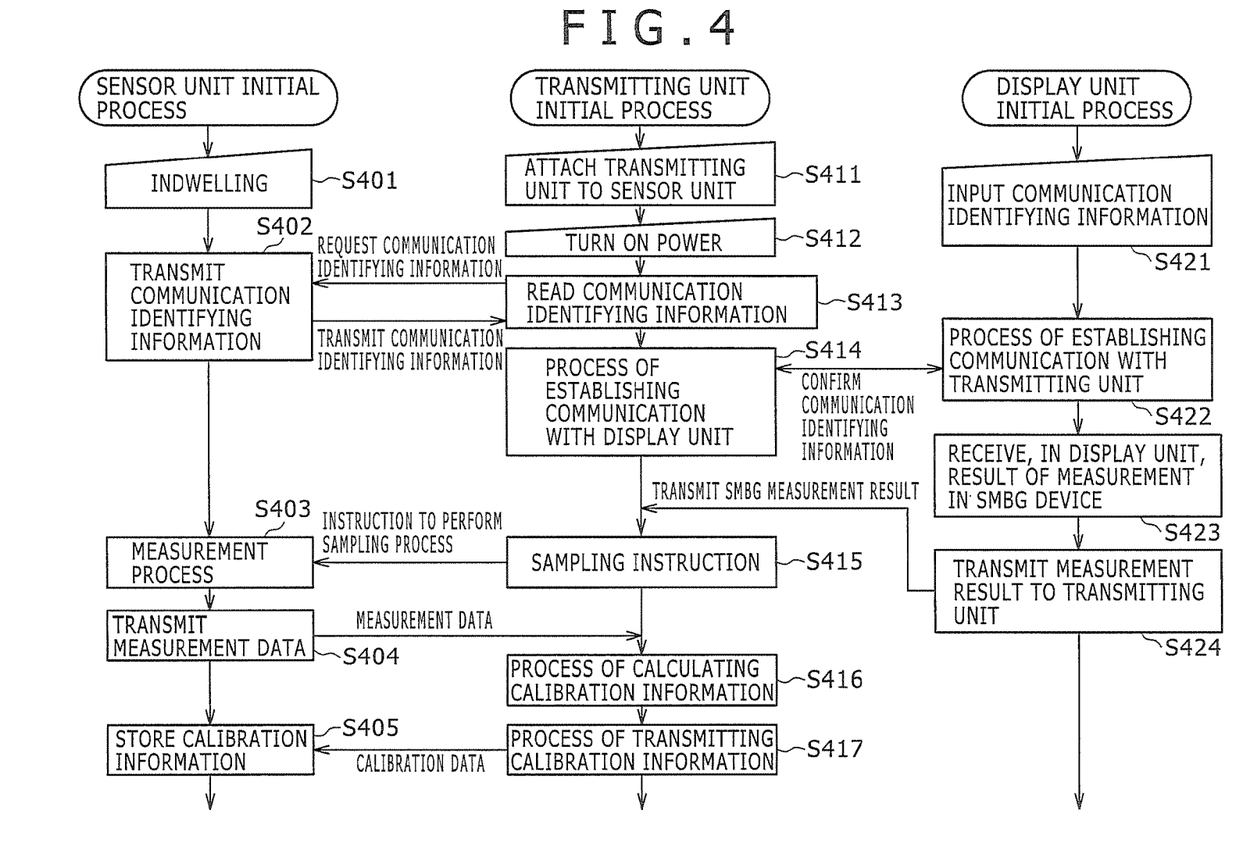
FIG. 4 is an illustration showing flow of an initial process in the body fluid component measuring system.

Description will first be made of a flow of the initial process in the body fluid component measuring system 100 according to the present embodiment. FIG. 4 is a flowchart of the flow of the initial process of each unit in the body fluid component measuring system 100 according to the present embodiment.

As shown in FIG. 4, in step S401, the sensor unit 110 is positioned indwelling in the subject. In step S411, the transmitting unit 120 is attached to the sensor unit 110. In step S421, communication identifying information (communication ID) necessary for communication between the transmitting unit 120 and the display unit 130 is input to the display unit 130. In step S412, the subject turns on the power to the transmitting unit 120 to activate the transmitting unit 120.

After the power to the transmitting unit 120 is turned on in step S412, the process proceeds to step S413, where the transmitting unit 120 attached to the sensor unit 110 requests communication identifying information from the sensor unit 110. Receiving the request for the communication identifying information, the sensor unit 110 in step S402 transmits the communication identifying information stored in the IC chip 113 in advance to the transmitting unit 120.

Thus reading the communication identifying information stored in the sensor unit 110 in advance at the time of the activation, the transmitting unit 120 establishes communication with the display unit 130 using the read communication identifying information (step S414 and step S422). Specifically, the communication identifying information is mutually verified, and when the communication identifying information matches, the communication is started. When the communication identifying information does not match, on the other hand, the communication is not performed. When the communication is not established, an error message indicating that the communication is not established can be output.

Establishing communication with the transmitting unit 120, the display unit 130 proceeds to step S423, where the display unit 130 receives a measurement result measured in advance in an SMBG device. For example, a user measures blood glucose level with a SMBG device and inputs the measurement result into the display unit 130 (step S423). Receiving the measurement result measured in advance in the SMBG device, the display unit 130 proceeds to step S424, where the display unit 130 transmits the received SMBG measurement result to the transmitting unit 120. That is, after the input of the measurement result into the display unit 130, the display unit 130 transmits the measurement result to the transmitting unit 120 (step S424).

Receiving the SMBG measurement result from the display unit 130, the transmitting unit 120 proceeds to step S415, where the transmitting unit 120 gives the sensor unit 110 an instruction to perform a sampling process for generating calibration information. Receiving the instruction to perform the sampling process, the sensor unit 110 performs a measurement process in step S403, and transmits measurement data to the transmitting unit 120 in step S404.

Receiving the measurement data from the sensor unit 110, the transmitting unit 120 proceeds to step S416, where the transmitting unit 120 calculates calibration information from the received measurement data and the SMBG measurement result. Further, the transmitting unit 120 proceeds to step S417, where the transmitting unit 120 transmits the calculated calibration information to the sensor unit 110.

The sensor unit 110 to which the calibration information is transmitted from the transmitting unit 120 proceeds to step S405, where the sensor unit 110 stores the calibration information in the memory of the IC chip 113 of the sensor unit 110. Next time and thereafter, each time the sensor unit 110 transmits measurement data, the sensor unit 110 transmits the stored calibration information to the transmitting unit 120 together with the measurement data.

<6. Flow of Monitoring Process>

Figure 5:
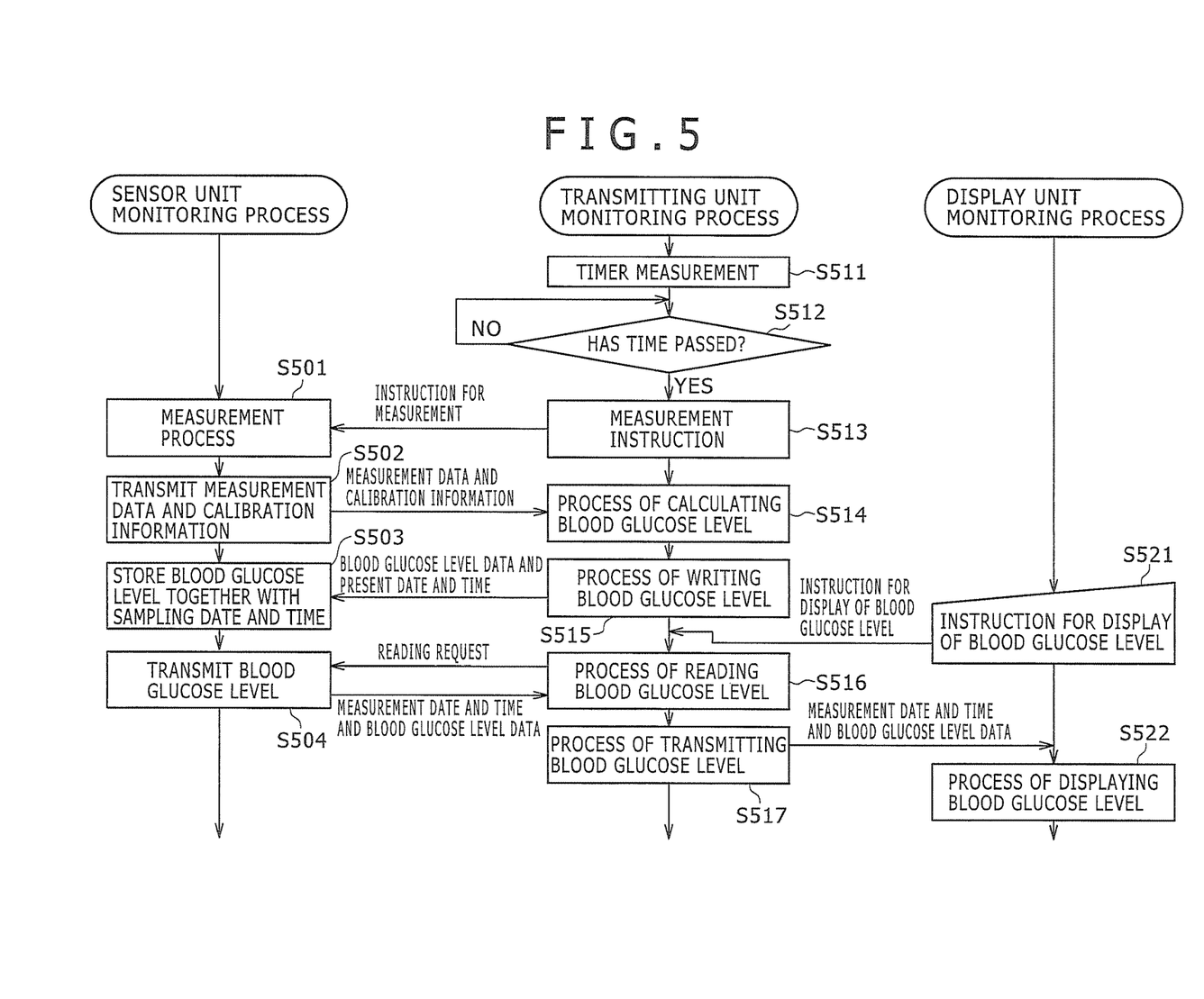
FIG. 5 is an illustration showing a flow of a monitoring process in the body fluid component measuring system.

Set forth next is a description of a flow of the monitoring process of the body fluid component measuring system 100 according to the present embodiment. FIG. 5 is a flowchart of the flow of the monitoring process of the body fluid component measuring system 100 according to the present embodiment.

As shown in FIG. 5, in step S511, timer measurement is started. In step S512, the CPU 222 in the transmitting unit 120 determines whether or not a predetermined time has passed. When it is determined in step S512 that the predetermined time has passed, the process proceeds to step S513, where the transmitting unit 120 gives a measurement instruction to the sensor unit 110. Thereby the measurement instruction is transmitted from the transmitting unit 120 at predetermined time intervals.

Receiving the measurement instruction from the transmitting unit 120, the sensor unit 110 performs a measurement process in step S501. Further, in step S502, the sensor unit 110 transmits measurement data obtained as a result of the measurement process to the transmitting unit 120 together with the calibration information stored in advance in the memory of the IC chip 113 in the initial process.

Receiving the measurement data and the calibration information from the sensor unit 110, the transmitting unit 120 in step S514 calculates blood glucose level data on the basis of the received measurement data and the received calibration information. Further, in step S515, the transmitting unit 120 transmits the calculated blood glucose level data in association with a present date and time to the sensor unit 110.

Receiving the blood glucose level data and the present date and time from the transmitting unit 120, the sensor unit 110 stores the present date and time as a measurement date and time in association with the blood glucose level data in the memory of the IC chip 113.

The calibration information stored in the initial process is thus transmitted together with the measurement data. Thus, even when the transmitting unit 120 is replaced, the calibration information used in the blood glucose level calculating process in the transmitting unit 120 before the replacement can be inherited as it is. That is, the calibration information used in the blood glucose level calculating process in the transmitting unit 120 before the replacement is available after the transmitting unit 120 is replaced.

Further, in step S521, when the display unit 130 receives a blood glucose level display instruction from the subject, the display unit 130 transmits the blood glucose level display instruction to the transmitting unit 120. Receiving the blood glucose level display instruction, the transmitting unit 120 performs a blood glucose level reading process in step S516. Specifically, the CPU 222 transmits a reading request to the sensor unit 110. Receiving the reading request from the transmitting unit 120, the sensor unit 110 in step S504 transmits the blood glucose level data stored in the memory of the IC chip 113 to the transmitting unit 120 together with the measurement date and time.

The blood glucose level data and the measurement date and time transmitted from the sensor unit 110 are transmitted to the display unit 130 by the transmitting unit 120 in step S517. The blood glucose level data and the measurement date and time transmitted by the transmitting unit 120 are displayed on the display unit 130 in step S522.

Thus, each time the transmitting unit 120 calculates blood glucose level data, the calculated blood glucose level data is stored in the sensor unit 110 in association with a measurement date and time. Therefore, even when the transmitting unit 120 is replaced, the blood glucose level data calculated before the replacement can be displayed on the display unit 130 together with the measurement date and time at a desired time.

<7. Flow of Replacement Process>

Figure 6:
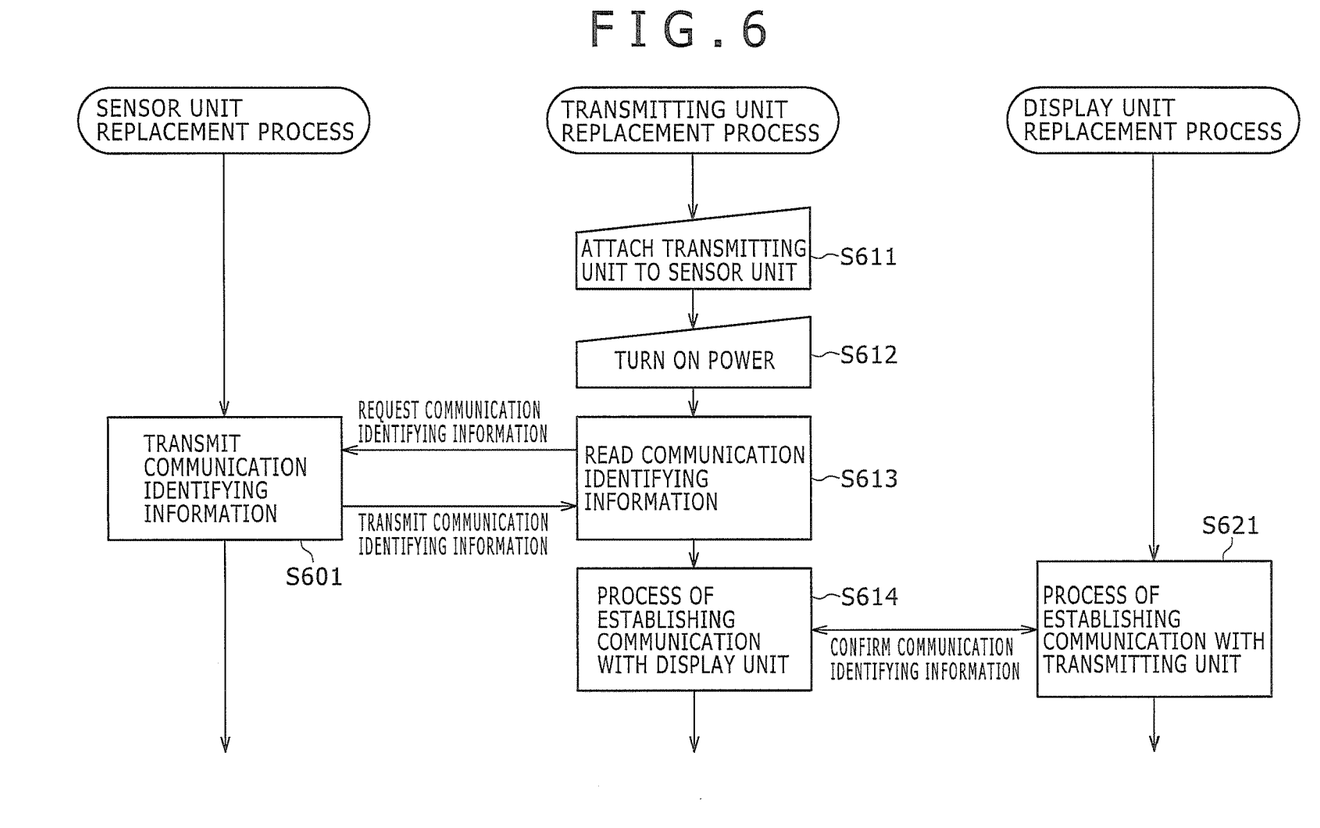
FIG. 6 is an illustration showing flow of a replacement process in the body fluid component measuring system.

Referring to FIG. 6, a flow of the replacement process of the body fluid component measuring system 100 according to the present embodiment will next be described. As shown in FIG. 6, in step S611, a new transmitting unit 120 is attached to the sensor unit 110. In step S612, the subject turns on power to the new transmitting unit 120. After the transmitting unit 120 is activated, the process proceeds to step S613.

In step S613, the transmitting unit 120 performs a process of reading communication identifying information stored in the sensor unit 110 in advance.

Specifically, at the time of the activation, a request for the communication identifying information is made to the sensor unit 110. Receiving the request for the communication identifying information from the transmitting unit 120, the sensor unit 110 in step S601 transmits the communication identifying information stored in the memory section to the transmitting unit 120. Receiving the communication identifying information from the sensor unit 110, the transmitting unit 120 in step S614 establishes communication with the display unit 130 using the information. Specifically, the communication identifying information used when communication was performed between the display unit 130 and the transmitting unit 120 before replacement and the communication identifying information read from the sensor unit 110 by the transmitting unit 120 after the replacement are compared with each other. The communication is established when the communication identifying information used when communication was performed between the display unit 130 and the transmitting unit 120 before the replacement and the communication identifying information read from the sensor unit 110 by the transmitting unit 120 after the replacement match each other. On the other hand, the communication is not performed or established when the communication identifying information used when communication was performed between the display unit 130 and the transmitting unit 120 before the replacement and the communication identifying information read from the sensor unit 110 by the transmitting unit 120 after the replacement do not match each other.

Thus, the communication identifying information between a transmitting unit 120 and the display unit 130 is stored in the sensor unit 110, and when the transmitting unit 120 is replaced, a transmitting unit 120 reads the communication identifying information stored in the sensor unit 110. Therefore, the communication identifying information is inherited even when the transmitting unit 120 is replaced.

Thereby, the workload on the subject at the time of replacement of the transmitting unit 120 can be reduced, and a replacement time when the transmitting unit 120 is replaced can be shortened. That is, the time during which continuous monitoring of the blood glucose level is interrupted can be shortened.

As is clear from the above description, in the body fluid component measuring system according to the present embodiment, the capacity of the secondary battery included in the transmitting unit 120 is minimized to reduce the weight and size of the transmitting unit 120 and improve the convenience of the subject.

In addition, in order to prevent the frequency of interruption of continuous monitoring of the blood glucose level from being thereby increased and prevent the cumulative value of interruption time from being thereby increased, a plurality of transmitting units are prepared, and the use and charging of the transmitting units are repeated alternately.

Further, in order to reduce a decrease in convenience which decrease is attendant on replacement of the transmitting unit and reduce a workload at the time of the replacement, various kinds of information to be inherited upon the transmitting unit 120 being replaced is stored in the sensor unit 110, and the transmitting unit 120 after the replacement is reads the various kinds of information from the sensor unit 110 as required.

As a result, the calibration information set during the indwelling time of the sensor unit 110 is inherited even when the transmitting unit 120 is replaced. It is thus unnecessary to input information necessary to calculate the calibration information again at the time of replacement of the transmitting unit.

In addition, blood glucose level data calculated in the transmitting unit 120 before replacement is inherited even when the transmitting unit 120 is replaced. Even after the replacement, the blood glucose level data before the replacement can be read and displayed on the display unit 130 by similar operation to that before the replacement.

Further, the communication identifying information between the transmitting unit 120 and the display unit 130 is inherited even when the transmitting unit 120 is replaced. It is thus unnecessary to set the communication identifying information again at the time of replacement of the transmitting unit 120.

That is, the time of interruption of monitoring of the blood glucose level, which interruption time is attendant on the replacement of the transmitting unit 120, can be shortened without impairing the convenience of the subject.

In the first embodiment described above, a description of a particular communication system between the transmitting unit 120 and the display unit 130 is set forth. The communication system between the transmitting unit 120 and the display unit 130 in the first embodiment can be a system using electromagnetic waves, but is not limited to this. For example, various known communication systems such as a system using electromagnetic induction, human body communication, proximity or vicinity noncontact communication, and the like can be used.

In addition, in the first embodiment, the sensor unit 110 and the transmitting unit 120 perform proximity communication using the IC tag, but are not limited to this. The transmitting unit and the sensor unit may be electrically connected to each other by using a metal contact or the like.

In addition, in the foregoing first embodiment, two transmitting units 120 are used. However, the present invention is not limited to this. It is possible to use three or more transmitting units 120.

Further, in the first embodiment described above, blood glucose level data is transmitted from the transmitting unit 120 to the display unit 130 only when there is a blood glucose level display instruction from the display unit 130. However, the present invention is not limited to this. Each time the transmitting unit 120 calculates blood glucose level data, the blood glucose level data may be transmitted to the display unit 130 in parallel with the writing of the blood glucose level data to the sensor unit 110.

The detailed description above describes an embodiment of a body fluid component measuring system representing one example of the body fluid component measuring system disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A body fluid component measuring system comprising:
a display device;
a sensor unit attachable to a body of a subject, the sensor unit comprising: a needle possessing a point configured to be indwelled in skin of the subject when the sensor unit is attached to the body of the subject to obtain a body fluid sample of the subject; a component measuring section which is connected to the needle to receive the body fluid sample obtained by the needle and which is configured to measure a predetermined body fluid component of the body fluid sample; and a memory which stores calibration information; and
a transmitting unit configured to receive the calibration information from the sensor unit in response to sending a measurement instruction to the sensor unit and comprising: a housing detachably attachable to the sensor unit; memory storing a calculating program which calculates a concentration of the predetermined body fluid component included in the body fluid sample based on the predetermined body fluid component of the body fluid sample measured by the component measuring section and the calibration information received from the sensor unit; and a transmitter which is configured to transmit a result of the calculation of the concentration of the predetermined body fluid component and a measurement date and time of the component to the display device which displays the concentration of the predetermined body fluid component and the measurement date and time of the component; wherein
the memory of the sensor unit stores identifying information, the transmitting unit is configured to, when activated, transmit a request to the sensor unit to read the identifying information stored in the memory of the sensor unit, and the transmitting unit is configured to establish communication with the display device using the identifying information read from the memory of the sensor unit,
the memory of the sensor unit stores the concentration of the predetermined body fluid component calculated by the calculating program stored in the memory of the transmitting unit and the measurement date and time of the component, and
the system further comprises a second transmitting unit detachably attachable to the sensor unit in place of the transmitting unit and configured to receive from the sensor unit, upon replacing the transmitting unit, the concentration of the predetermined body fluid component calculated by the transmitting unit, the measurement date and time of the component, and the calibration information.

2. The body fluid component measuring system according to claim 1, wherein the memory of the sensor unit is an integrated circuit chip.

3. The body fluid component measuring system according to claim 1, wherein the transmitting unit includes a speaker providing audible notifications.

4. The body fluid component measuring system according to claim 1, wherein the transmitting unit includes a rechargeable battery.

5. A body fluid component measuring system comprising:
a sensor unit configured to be at least partially positioned indwelling in skin of a subject, the sensor unit configured to measure a predetermined body fluid component of an actual body fluid of the subject to obtain a measurement signal and to store calibration information; and
a transmitting unit comprising a housing detachably attachable to the sensor unit and activated by a user, the transmitting unit configured to receive the measurement signal and the calibration information from the sensor unit in response to sending a measurement instruction to the sensor unit, to perform calculation of a concentration of the body fluid component in a body fluid which is either a same kind as the actual body fluid or a different kind from the actual body fluid, on a basis of the received measurement signal and the received calibration information, and to transmit a result of the calculation to a display device; wherein
the sensor unit stores identifying information for establishing communication between the transmitting unit and the display device and the concentration of the predetermined body fluid component calculated by the transmitting unit and a measurement date and time of the component;
the transmitting unit is configured to, when activated, transmit a request to the sensor unit to read the identifying information stored in the sensor unit and to establish communication with the display device using the read identifying information; and
the system further comprises a second transmitting unit detachably attachable to the sensor unit in place of the transmitting unit and configured to receive from the sensor unit, upon replacing the transmitting unit, the concentration of the predetermined body fluid component calculated by the transmitting unit, the measurement date and time of the component, and the calibration information.

6. The body fluid component measuring system according to claim 5, wherein the sensor unit is configured to perform a sampling measurement process to produce measurement data, and to transmit the measurement data to the transmitting unit for calculating the calibration information.

7. The body fluid component measuring system according to claim 6, wherein the transmitting unit is configured, when it has received the measurement data from the sensor unit, to calculate the calibration information using the measurement data received from the sensor unit, and to store the calculated calibration information in the sensor unit.

8. The body fluid component measuring system according to claim 7, wherein the sensor unit is configured to measure the predetermined body fluid component of the body fluid of the subject at predetermined time intervals, and wherein the transmitting unit is configured, when it receives from the sensor unit the measurement signal measured at the predetermined time intervals, to also read the stored calibration information.

9. The body fluid component measuring system according to claim 8, wherein the concentration of the body fluid component is a blood glucose level, and wherein the transmitting unit is configured to calculate the blood glucose level based on the measurement signal and the calibration information received from the sensor unit, and to store the calculated blood glucose level in the sensor unit together with the measurement date and time of the component.

10. The body fluid component measuring system according to claim 9, wherein the transmitting unit is configured to receive an instruction to read blood glucose level data from the display device, and, when it receives the instruction to read the blood glucose level data from the display device, to read the blood glucose level data stored in the sensor unit together with the measurement date and time of the component, and to transmit the blood glucose level data to the display device together with the measurement date and time of the component.

11. The body fluid component measuring system according to claim 5, wherein the transmitting unit operates on a rechargeable battery.

12. A method of measuring a body fluid component comprising:

when activated, transmitting a request to read communication identification information stored in a sensor unit with a transmitting unit, the transmitting unit comprising a housing detachably mounted on the sensor unit;

verifying, with the transmitting unit, that the communication identification information read from the sensor unit matches communication identification information in a display device to establish communication between the transmitting unit and the display device, the display device including a display which displays information;

obtaining a body fluid sample of a subject which contains the body fluid component with a sensor unit;

measuring, with the sensor unit, the body fluid component of the body fluid sample and sending, from the sensor unit to the transmitting unit, in response to the transmitting unit sending a measurement instruction to the sensor unit, measurement data indicating the measured body fluid component and calibration information;

calculating, with the transmitting unit, a concentration of the body fluid component based on the measurement data from the sensor unit and the calibration information from the sensor unit;

transmitting, with the transmitting unit, the calculated concentration of the body fluid component to the sensor unit and a measurement date and time of the component;

storing, with the sensor unit, the calculated concentration of the body fluid component and the measurement date and time of the component; and detachably attaching a second transmitting unit to the sensor unit in place of the transmitting unit which receives from the sensor unit, upon replacing the transmitting unit, the concentration of the predetermined body fluid component calculated by the transmitting unit, the measurement date and time of the component, and the calibration information.

13. The method according to claim 12, further comprising transmitting, with the transmitting unit, the calculated concentration of the body fluid component and the measurement date and time of the component to the display device, and displaying, with the display of the display device, the concentration of the body fluid component and the measurement date and time of the component.

14. The method according to claim 12, wherein the sensor unit measures the body fluid component of the body fluid sample in response to the measurement instruction from the transmitting unit.

15. The method according to claim 12, wherein the sensor unit sends the calibration information to the transmitting unit together with the measurement data.

* * * * *